US007972769B2

(12) United States Patent
Kornblith et al.

(10) Patent No.: US 7,972,769 B2
(45) Date of Patent: *Jul. 5, 2011

(54) METHOD FOR PREPARING CELL CULTURES FROM BIOLOGICAL SPECIMENS FOR CHEMOTHERAPEUTIC AND OTHER ASSAYS

(75) Inventors: Paul L. Kornblith, Pittsburgh, PA (US); Sheri Gimigliano, Pittsburgh, PA (US)

(73) Assignee: Precision Therapeutics, Inc., Pittsburgh, PA (US)

( * ) Notice: Subject to any disclaimer, the term of this patent is extended or adjusted under 35 U.S.C. 154(b) by 687 days.

This patent is subject to a terminal disclaimer.

(21) Appl. No.: 11/595,967

(22) Filed: Nov. 13, 2006

(65) Prior Publication Data

US 2007/0059821 A1      Mar. 15, 2007

Related U.S. Application Data

(62) Division of application No. 10/208,480, filed on Jul. 30, 2002, now abandoned.

(51) Int. Cl.
C12N 5/09 (2010.01)
C12Q 1/00 (2006.01)
(52) U.S. Cl. .......................... 435/4; 435/374; 436/64
(58) Field of Classification Search .................. None
See application file for complete search history.

(56) References Cited

U.S. PATENT DOCUMENTS

| | | | |
|---|---|---|---|
| 4,423,145 A | 12/1983 | Stampfer et al. | |
| 4,559,299 A | 12/1985 | Rotman | |
| 4,668,618 A | 5/1987 | Thornthwaite | |
| 4,816,395 A | 3/1989 | Hancock et al. | |
| 4,937,187 A | 6/1990 | Rotman | |
| 4,996,145 A | 2/1991 | Weisenthal | |
| 5,242,806 A | 9/1993 | Yen-Maguire et al. | |
| 5,270,172 A | 12/1993 | Morgan | |
| 5,403,574 A | 4/1995 | Piwnica-Worms | |
| 5,443,950 A | 8/1995 | Naughton et al. | |
| 5,585,265 A * | 12/1996 | Kahn et al. | 435/6 |
| 5,607,918 A | 3/1997 | Eriksson et al. | |
| 5,705,270 A | 1/1998 | Soon-Shiong et al. | |
| 5,728,541 A * | 3/1998 | Kornblith | 435/29 |
| 5,789,158 A | 8/1998 | Knowles et al. | |
| 5,874,218 A | 2/1999 | Drolet | |
| 5,888,765 A | 3/1999 | Patterson et al. | |
| 5,942,385 A | 8/1999 | Hirth | |
| 5,972,639 A | 10/1999 | Parandoosh | |
| 6,008,007 A | 12/1999 | Fruehauf et al. | |
| 6,020,473 A | 2/2000 | Keyt et al. | |
| 6,111,092 A | 8/2000 | Williamson | |
| 6,261,795 B1 | 7/2001 | Fruehauf et al. | |
| 6,303,324 B1 | 10/2001 | Fruehauf | |
| 6,335,170 B1 | 1/2002 | Orntoft | |
| 6,416,967 B2 * | 7/2002 | Kornblith | 435/29 |
| 6,511,806 B1 | 1/2003 | Fruehauf et al. | |
| 6,664,062 B1 | 12/2003 | Stanton, Jr. | |
| 6,887,680 B2 | 5/2005 | Kornblith | |
| 6,900,027 B1 | 5/2005 | Kornblith | |
| 6,933,129 B1 * | 8/2005 | Kornblith | 435/29 |
| 7,112,415 B2 | 9/2006 | Kornblith | |
| 7,314,731 B2 | 1/2008 | Kornblith | |
| 7,563,593 B2 | 7/2009 | Kornblith | |
| 7,575,868 B2 | 8/2009 | Kornblith et al. | |
| 7,829,288 B2 | 11/2010 | Kornblith et al. | |
| 2002/0168679 A1 | 11/2002 | Naus et al. | |
| 2002/0177147 A1 | 11/2002 | Mealey et al. | |
| 2003/0096290 A1 | 5/2003 | Fruehauf et al. | |
| 2003/0148345 A1 | 8/2003 | Kopreski | |
| 2004/0023375 A1 | 2/2004 | Kornblith et al. | |
| 2004/0072772 A1 | 4/2004 | Kornblith et al. | |
| 2004/0086888 A1 | 5/2004 | Kornblith et al. | |
| 2005/0004766 A1 | 1/2005 | Ramnarayan et al. | |

FOREIGN PATENT DOCUMENTS

| | | |
|---|---|---|
| EP | 0911389 A2 | 4/1999 |
| WO | WO 98/02038 A1 | 1/1998 |
| WO | WO 00/75287 | * 12/2000 |
| WO | WO 01/65994 | 9/2001 |
| WO | WO 01/79540 | 10/2001 |
| WO | WO 02/33117 | 4/2002 |
| WO | WO 2004/015065 | 2/2004 |
| WO | WO 2004/035833 | 4/2004 |

OTHER PUBLICATIONS

Freshney (The Culture of Animal Cells, 1994, pp. 292-296, 299, 351-352).*
Ness et al., Cell viability assay for drug testing in ovarian cancer: In vitro kill versus clinical response, Anticancer Research, 22(2B), pp. 1145-1149, (Mar. 2002), XP009082283.
Mothersill et al., Effect of radiation and other cytotoxic agents on the growth of cells cultured from normal and tumor tissues from the female genital tract, Gynecologic Oncology, 37(2), pp. 210-218, (1990), XP002429819.
Jung et al., A three-dimensional micro-organ culture system optimized for in vitro growth of human malignant brain tumors, Neurosurgery, 29(3), (1991), XP001055649.
Letwin, Chemosensitivity testing, Clinical Journal of Oncology Nursing, 5(5), pp. 195-200, (Sep. 2001), XP009082265.
Ochs et al., Evidence for the isolation, growth, and characterization of malignant cells in primary cultures of human tumors, In Vitro Cellular and Developmental Biology—Animal, 39(1-2), pp. 63-70, (2003), XP009082263.
Supplementary European Search Report based on International Appl. No. PCT/US2003/023888, (May 8, 2007).
PL Kornblith et al., "Response variability of human brain tumors to AZQ in tissue culture," Journal of Neuro-Onocology, 1986, pp. 49-54, vol. 4, Martinus Nijhoff Publishers, Boston.
RS Weinstein et al., "Ultrastructure of a cloned astrocytoma in tissue culture," Cancer, 1971, pp. 1174-1181, vol. 27.
PMcL Black et al., "Ultrastructural and electrophysiological features of meningioma whorls in tissue culture," Acta Neuropathol (Berl), 1979, vol. 46, pp. 33-38.
RM Scott et al., "Invasiveness in tissue culture: A technique for study of gliomas," Surg Forum, 1978, pp. 531-533, vol. 29.
T. Liszczak et al., "Morphological, biochemical, ultrastructural, tissue culture and clinical observations of typical and aggressive craniopharyngiomas," Acta Neuropathol (Berl), 1978, pp. 191-203, vol. 43.

(Continued)

Primary Examiner — Karen A Canella
(74) Attorney, Agent, or Firm — Cooley LLP

(57) ABSTRACT

An improved method for preparing a cell culture is disclosed. The method includes culturing a multicellular tissue explant in the presence of growth medium that is substantially free of enzymes capable of digesting the explant and, subsequently, removing the explant at a predetermined time.

21 Claims, No Drawings

OTHER PUBLICATIONS

PL Kornblith et al., "Growth-inhibitory effects of diphenylhydantoin on human brain tumor cells in culture," Neurosurgery, 1978, pp. 122-127, vol. 2.

RR Weichselbaum et al., "Characterization and radiobiologic parameters of medulloblastoma in vitro," Cancer, 1977, pp. 1087-1096, vol. 40.

RL Martuza et al., "Characteristics of human optic gliomas in tissue culture," J. Neurosurg, 1977, pp. 78-84, vol. 46.

MA Oberc-Greenwood, et al., "Ultrastructural features of the lymphocyte-stimulated halos produced by human glioma-derived derived cells in vitro," Journal of Neuro-Oncology, 1986, pp. 387-396, vol. 3.

BH Smith et al., "Membrane and cytoplasmic changes in 1,3-bis (2-chloroethy 1)- 1—nitrosourea (BCNU)-sensitive and resistant human malignant glioma-derived cell lines," Journal of Neuro-Oncology, 1983, pp. 237-248, vol. 1.

GA Curt et al., "Phase II and pharmacokinetic study of aziridinylbenzoquinone (2,5-diaziridinyl-3, 6-bis(carboethoxyamino)-1,4 benzoquinone, diaziquone, NSC 182986) in high grade gliomas," Cancer Research, 1983, pp. 6102-6105, vol. 43, Issue 12 pt 1.

N Shitara et al., "Flowcytometric and cytogenetic analysis of human cultured cell lines derived from high- and low-grade astrocytomas," Acta Neuropathol (Berl), 1983, pp. 40-48, vol. 60.

MK Gumerlock et al., "Chemical differentiation of cultured human glioma cells: Morphologic and immunologic effects," Surgical Forum, 1981, pp. 475-477, vol. XXXII.

PL Kornblith et al., "Growth-inhibitory effect of diphenylhydantoin on murine astrocytomas," Neurosurgery, 1979, pp. 259-263, vol. 5.

MC Trachtenberg et al., "Biophysical properties of cultured human glial cells," Brain Research, 1972, pp. 279-298, vol. 38.

J. Lightbody et al., "Biochemically differentiated clonal human glial cells in tissue culture," J. Neurobiology, 1970, pp. 411-417, vol. 1, No. 4.

PMcL Black et al., "Biophysical properties of human astrocytic brain tumor cells in cell nature," Journal of Cellular Physiology, 1980, pp. 565-570, vol. 105.

TM Liszczak et al., "Ultrastructure of human endometrial epithelium in monolayer culture with and without steroid hormones," In Vitro, 1977, pp. 344-356, vol. 13, No. 6.

TM Liszczak et al., "Procedure for the embedment and ultrastructural visualization of cells cultured on plastic microtest plates," Journal of Immunological Methods, 1977, pp. 131-134, vol. 15.

RM Stewart et al., "Glutamate accumulation by human gliomas and meningiomas in tissue culture," Brain Research, 1976, pp. 441-452, vol. 118.

PL Kornblith et al., "The future of therapy for glioblastoma," Surg Neurol, 1993, pp. 538-543, vol. 39.

PL Kornblith, "Management of malignant gliomas," Neurosurgery Quarterly, 1991, pp. 97-110, vol. 1, Issue 2.

PL Kornblith et al., "Chemotherapy for malignant gliomas," Journal of Neurosurgery, 1988, pp. 1-17, vol. 68, Issue 1.

PE McKeever et al., "Products of cells cultured from gliomas: VI. Immunofluorescent, morphometric, and ultrastructural characterization of two different cell types growing from explants of human gliomas," American Journal of Pathology, 1987, pp. 358-372, vol. 127, Issue 2.

PMcL Black et al., "Immunological, biological, ultrastructural, and electrophysiological characteristics of a human glioblastoma-derived cell culture line," J. Neurosurg., 1982, pp. 62-72, vol. 56.

PL Kornblith, "The role of cytotoxic chemotherapy in the treatment of malignant brain tumors," Surg Neurol, 1995, pp. 551-552, vol. 44.

WC Welch et al., "Morphologic immunologic, biochemical and cytogenetic characteristics of the human glioblastoma-derived derived cell line, SNB-19," Journal of the Society for in Vitro Biology, 1995, pp. 610-616, vol. 31.

E Sariban et al., "DNA crosslinking responses of human malignant glioma cell strains to chloroethylnitrosoureas, cisplatin and diaziquone," Cancer Research, 1987, pp. 3988-3994, vol. 47, Issue 15.

Meisel et al., How to manage individualized drug therapy : Application of pharmacogenetic knowledge of drug metabolism and transport. Clinical Chemistry and Laboratory Medicine 2000, 38(9) : 869-876.

Nauck et al., Rapid detection of the C3435T polymorphism of multidrug resistance gene 1 using fluorogenic hybridization probes. Clinical Chemistry 2000, 46(12) : 1995-1997.

Pastinen et al., Minisequencing: A spefici tool for DNA analysis and diagnostics on oligonucleotide arrays. Genome Research 1997, 7 : 606-614.

Broadley, et al. (1995) "A tissue culture method for the study of canine vocal fold fibroblasts," Laryngoscope, 105:23-27.

Dudley et al. (1992) "A human endometrial explant system: Validation and potential applications," Am. J. Obstet. Gynecol. 167(6):1774-1780.

Gerweck et al. (1977) "Radiation sensitivity of cultured human glioblastoma cells," Radiology, 125(1):231-234.

Ghosh, et al. (1987) "Immunohistological staining of reactive mesothelium, mesothelioma, and lung carcinoma with a panel of monoclonal artibodies," J. Clin. Pathol. 40:19-25.

Kitamura, et al. (1995) "Chemosensitivity of gastric cancer using adhesive tumor cell culture system," Oncol. Rep. 2:27-31.

Nance, et al. (1991) "Immunocytochemical panel for the identification of malignant cells in serious effusions," Am. H, Clin. Pathol. 95(6):867-874.

Pinkus, et al. (1985) "Optimal Immunoreactivity of keratin proteins in formalin-fixed, paraffin-embedded tissue requires preliminary trypsinization," J. Histochem. Cytochem.33(5):465-473.

Raju, (1990) "The histological and immunohistochemical evidence of squamous metaplasia from the myoepithelial cells in the breast," Histopathol. 17(3):272-275.

Singh et al. (1995) "Significance of epithelial membrane antigen in the work-up of problematic serous effusions," Diagnostic cytopathol. 13(1):3-7.

Stoop, et al. (1992) "Identification of malignant cells in serous effusions using a panel of monoclonal antibodies Ber-EP4, MCA-b-12 and EMA" Cytopathol. 3:297-302.

Tannock, et al. (1992) *The basic science of oncology*, $2^{nd}$ Ed. pp. 247-246, 261-248, 261-265, 303-306.

Wiseman, (1976) "A modification of hepatest, using the Terasaki plate, for the detection of HBAg in blood donors," J. Clin. Pathol., 29(3):264-266.

Alley (1991) "Morphometric and colorimetric analyses of human tumor cell line growth and drug sensitivity in soft agar culture," Cancer Res. 51:1247-1256.

Andreotti (1994) "TCA-100 tumor chemosensitivity assay: differences in sensitivity between cultured tumour cell lines and clinical studies," J. Biolumin Chemilumin, 9:373-378.

Arnold et al. (1995) "Evaluation of chemoprotective agents in different mechanistic classes using a rat tracheal epithelial cell culture transformation assay," Cancer Res. 55:537-543.

Burczynski, et al. (2000) "Toxicogenomics-based discrimination of toxic mechanism in HepG2 human hepatoma cells," Toxicoloical Sciences, 58(2):399-415.

Dietel et al. (1993) "In Vitro prediction of cytostatic drug resistance in primary cell cultures of solid malignant tumours," Eur. J. Cancer 29A(3):416-420.

Frykholm, et al. (1991) "Heterogeneity in antigenic expression and radiosensitivity in human colon carcinoma cell lines" In Vitro Cell Dev. Biol., 27A:900-906.

Fulda, et al. (1995) "Antiproliferative potential of cytostatic drugs on neuroblastoma cells in vitro," Eur J. Cancer 34A(4):616-621.

Gamboa et al. (1995) "Characterization and development of UCI 107, a primary human ovarian carcinoma cell line," Gynecologic Oncology, 58:336-343.

Goldsworthy et al. (1993) "Concepts, labeling procedures and design of cell proliferation studies relating to carcinogenesis," Environmental Health Perspectives, 101(Suppl. 5):59-66.

Hoffman, (1994) "The three-dimensional question: can clinically relevant tumor drug resistance be measured in vitro?" Cancer and Metastasis Reviews, 13(2):169-173.

Kaaijk et al. (1996) "Daunorubicin and doxorubicin but not BCNU have deleterious effects on organotypic multicellular spheroids of gliomas," Brittish J. Cancer, 74(2):187-193.

Kornblith, (1978) "Role of tissue culture in prediction of malignancy," Clin. Neurosurg. 25:346-376.

Kornblith (1978) "Variations in repsonse of human brain tumors to BCNU in vitro," J. Neurosurg, 48(4):580*586.

Kruczynski et al. (1993) "Evidence of a direct relationship between the increase in the in vitro passage number of human non-small-cell-lung cancer primocultures and their chemosensitivity," Anticancer Res. 13:507-514.

Persons, et al. (1993) "Interphase molecular cytogenic analysis of epithelial ovarian carcinomas," Am. J. Pathol. 142(3):733-741.

Zwergel, et al. (1998) "A new serial transfer explant cell culture system for human prostatic cancer tissues preventing selection toward diploid cells," Cancer Genet. Cytogenet. 101:16-23.

* cited by examiner

METHOD FOR PREPARING CELL CULTURES FROM BIOLOGICAL SPECIMENS FOR CHEMOTHERAPEUTIC AND OTHER ASSAYS

REFERENCE TO RELATED APPLICATIONS

This application is a divisional of U.S. Ser. No. 10/208,480, filed Jul. 30, 2002, which is hereby incorporated by reference in its entirety.

FIELD OF THE INVENTION

The invention relates to methods for the preparation of a cell culture monolayer, and more particularly to methods for the preparation of a tumor cell culture monolayer that substantially comprises tumor cells.

BACKGROUND

Prior to approval for medical use in the United States, all pharmaceutical agents are subjected to rigorous testing for efficacy and safety. Typically, methods of assessing the efficacy of a pharmaceutical agent include complex studies of pooled patient samples or pooled data, and statistical interpretation of the results. The conclusions that follow such studies are inherently generalized or averaged over the subject patient population. With pharmaceutical agents, however, and particularly with cancer chemotherapeutic agents, the efficacy of an agent in treating an individual patient can vary greatly from the generalized data, often to the detriment of the individual patient. The need has long been recognized for a method of assessing the therapeutic potential of pharmaceutical agents, including but not limited to chemotherapeutic agents, for their specific efficacy in an individual patient.

Assays exist which expose malignant tissue of various types to pharmaceutically-active agents for the purpose of assessing the best choice for therapeutic administration. For example, in Kruczynski, A., et al., "Evidence of a direct relationship between the increase in the in vitro passage number of human non-small-cell lung cancer primocultures and their chemosensitivity," *Anticancer Research*, vol. 13, no. 2, pp. 507-513 (1993), chemosensitivity of non-small-cell lung cancers was investigated in in vivo grafts, in in vitro primocultures, and in commercially available cancer cell lines. The increase in chemosensitivity was documented and correlated with morphological changes in the cells in question. Often, animal model malignant cells and/or established cell cultures are tested with prospective therapy agents, see for example Arnold, J. T., "Evaluation of chemopreventive agents in different mechanistic classes using a rat tracheal epithelial cell culture transformation assay," *Cancer Res., vol.* 55, no. 3, pp. 537-543 (1995).

According to prior art methods of using specific patient tumor cells to form an in vitro assay particular to that patient, the cells are harvested (biopsied) and trypsinized (connective tissue digested with the enzyme trypsin) to yield a cell suspension suitable for conversion to the desired tissue culture form. The in vitro tissue culture cell preparations which result from these prior art methods typically fail to accurately replicate the chemosensitivity of the original tumor or other cell biopsy. This inability arises, in part, because the heterogeneity of cell population in the tumor tissue has been disturbed in culture, or entirely obliterated such that the cell culture preparation is essentially monoclonal. Moreover, prior art methods of culturing actual patient tissue samples inevitably result in cell cultures with a significant level of non-target cells, such as fibroblasts or other stromal cells, which have a tendency to outgrow the target tumor cells in a cell culture. Furthermore, standard cloning and tissue culture techniques are complicated and expensive for use in individualized patient testing. Thus, a need remains for improved and efficient methods of cell culture preparation that provide a heterogeneous cell population that substantially comprises target cells from a particular patient. Such a cell culture preparation is useful in drug or chemotherapeutic agent screening to provide information indicative of the in vivo reactivity of the cells, and thus the specific efficacy as to a particular patient.

SUMMARY OF THE INVENTION

The present invention provides methods for preparing a cell culture from a multicellular tissue extract. Cell cultures of the invention have the advantage of closely resembling the in vivo cell population from which they were obtained, thus providing an accurate and reliable proxy for the cell population in vivo. For example, a tumor cell culture of the invention comprises a population of cells that mimics the tumor cell population in the patient from whom a tissue explant is obtained. This allows chemosensitivity and chemoresistivity testing that is highly-reliable in predicting the effects of therapeutic agents on the tumor in vivo. The invention is based, in part, on the insight that timely removal of a cellular explant from culture results in a culture that is highly indicative of in vivo cell population. The invention provides further benefits recognized by culturing tissue explants in a growth medium that is essentially free of digestive enzymes.

Accordingly, in one aspect, the invention provides a cell culture system in which a multicellular tissue explant is placed in a growth medium and is removed from the growth medium at a predetermined time. The explant is removed prior to the emergence from the explant of a substantial number of non-target cells, resulting in a monolayer of cells that is enriched for the cell population of interest. For example, it has been discovered that cells emerge as a monolayer from a cultured tumor tissue explant in an orderly fashion, the tumor cells emerging first, followed by stromal cell populations. If the tumor cell explant remains in culture, the stromal cells have been found to dominate the tumor cells in culture. This creates a culture that is enriched from non-target stromal cells and that is not reflective of the in vivo cell population. Thus, in a tumor cell culture, the explant is removed from the growth medium prior to the emergence of a substantial number of stromal cells from the explant. This provides a cell culture monolayer that is predominantly composed of tumor cells. It has also been discovered that the cell cultures described above produce optimal results in cell culture medium that is essentially free of digestive enzymes.

The time at which an explant is removed from its culture medium depends upon the type of cells being cultured, the rate of emergence of various cell types, and the desired purity of the resulting cell culture monolayer. This can be determined empirically for a given cell type. In the case of tumor cells, the multicellular tissue explant is preferably removed when the cell culture monolayer is at about 10 to about 50 percent confluency. In a preferred embodiment, the multicellular tissue explant is removed at about 15 to about 25 percent confluency. In a particularly preferred embodiment, the explant is removed at about 20 percent confluency.

The invention further comprises the preparation of a cell suspension from the cell culture monolayer. A tissue explant is cultured in an appropriate medium and is removed at a predetermined time, resulting in a monolayer enriched for the cells of interest. A suspension is then made from the monolayer and cells of the suspension are inoculated into at least one segregated site. In one embodiment, a chemosensitivity assay is performed on the inoculated cell suspension by exposing the segregated site to at least one agent and assessing the chemosensitivity of the cells in the segregated site. Chemoresistivity assays are similarly performed.

In another embodiment, the invention provides methods for determining the chemosensitivity of a tissue in a patient by determining the chemosensitivity of a cell culture preparation from the patient. In yet another embodiment, the invention provides methods for identifying an agent having anti-tumorogenic effect in a patient by assessing the chemosensitivity of segregated sites of cells from a tumor cell culture prepared according to the invention.

DETAILED DESCRIPTION OF THE INVENTION

The present invention provides methods for preparing a cell culture monolayer by culturing a tissue sample from a patient. Ultimately, the culture may be used to screen at least one candidate therapeutic or chemotherapeutic agent for efficacy as to a specific patient, in which a tissue sample from the patient is harvested and separately exposed to a plurality of treatments and/or therapeutic agents for the purpose of objectively identifying the chemosensitivity or chemoresistivity of the tissue sample and the best treatment or agent for the patient. Tissue sample preparation techniques render this method practically as well as theoretically useful. According to the invention, the initial cohesive multicellular particulates (explants) of the tissue sample are prepared mechanically, rather than enzymatically, for initial tissue culture monolayer preparation. The multicellular tissue explant is removed from the culture growth medium at a predetermined time to both allow for the growth of target cells and prevent substantial growth of non-target cells such as fibroblasts or stromal cells.

An important application of the present invention is the screening of chemotherapeutic agents and other antineoplastic or anti-tumorogenic therapies against tissue culture preparations of tumorogenic cells from the patient from whom the sample is biopsied. Related anti-cancer therapies which can be screened using the methods of the invention are both radiation therapy and agents which enhance the cytotoxicity of radiation, as well as immunotherapeutic anti-cancer agents. Screening processes for treatment or therapeutic agents for nonmalignant syndromes are also embraced within this invention, however, and include without limitation, agents which combat hyperproliferative diseases, such as psoriasis, or wound healing agents. Nor is the present efficacy assay limited only to the screening of active agents which speed up (healing) or slow down (anti-cancer, anti-hyperproliferative) cell growth because agents intended to enhance or to subdue intracellular biochemical functions may be tested in the present tissue culture system as well. For example, the formation or blocking of enzymes, neurotransmitters and other biochemicals may be, screened with the present assay methods prior to treatment of the patient.

By way of example, in one embodiment of the invention, a cell culture monolayer in accordance with the invention is prepared using the following procedure. Many aspects of the following procedure may be altered as necessary and as well known in the art. A biopsy of non-necrotic, non-contaminated tissue is harvested from the patient by any suitable biopsy or surgical procedure known in the art. In a preferred embodiment, the tissue sample is tumor tissue. In one embodiment, the biopsy is at least about 100 mg. Biopsy sample-preparation generally proceeds under sterile conditions. Cohesive multicellular particulates (explants) are prepared from the tissue sample using mechanical fragmentation. In one embodiment, this mechanical fragmentation of the explant occurs in a medium substantially free of enzymes that are capable of digesting the explant. In a preferred embodiment, the tissue sample is minced with sterile scissors to prepare the explants. In a particularly preferred embodiment, the tissue sample is systematically minced by using two sterile scalpels in a scissor-like motion, or mechanically equivalent manual or automated opposing incisor blades. This cross-cutting motion creates smooth cut edges on the resulting tissue multicellular particulates. In one embodiment, multicellular particulates measuring about 1 mm$^3$ may be produced. After the tissue sample has been minced, the particles are plated in culture flasks (for example, 9 explants per T-25 or 20 particulates per T-75 flask). The explants may be evenly distributed across the bottom surface of the flask, followed by initial inversion for about 10-15 minutes. The flask may then be placed in a non-inverted position in a 37° C. $CO_2$ incubator for about 5-10 minutes. In another embodiment in which the tissue sample comprises brain cells, the flasks are placed in a 35° C., non-$CO_2$ incubator. Flasks should be checked regularly for growth and contamination. According to a preferred embodiment of the invention, the multicellular explant is removed from the cell culture at a predetermined time, as described below. Over a period of a few weeks a monolayer will be produced. With respect to the culturing of tumor cells, it is believed (without any intention of being bound by the theory) that tumor cells grow out from the multicellular explant prior to stromal cells. Thus, by initially maintaining the tissue cells within the explant and removing the explant at a predetermined time, growth of the tumor cells (as opposed to stromal cells) into a monolayer is facilitated.

The use of the above procedure to form a cell culture monolayer culture maximizes the growth of tumor cells from the tissue sample, and thus optimizes ensuing tissue culture assay of various agents (e.g., chemotherapeutic agents) to be tested. Once a primary culture and its derived secondary monolayer tissue culture has been initiated, the growth of the cells may be monitored to oversee growth of the monolayer and ascertain the time to initiate the chemotherapy assay and to determine the growth rate of the cultured cells. Prior to the chemotherapy assay, monitoring of the growth of cells may be conducted by visual monitoring of the flasks on a periodic basis, without killing or staining the cells and without removing any cells from the culture flask. Data from periodic counting is then used to determine growth rates which may or may not be considered parallel to growth rates of the same cells in vivo in the patient. If growth rate cycles can be documented, for example, then dosing of certain active agents can be customized for the patient. The same growth rate can be used to evaluate radiation treatment periodicity, as well. It should be noted that with the growth rate determinations conducted while the monolayers grow in their flasks, the present method requires no hemocytometry, flow cytometry or use of microscope slides and staining, with all their concomitant labor and cost.

Monolayer growth rate may be monitored using, for example, a phase-contrast inverted microscope. In one embodiment, culture flasks are incubated in a (5% $CO_2$) incubator at about 37° C. The flask is placed under the phase-contrast inverted microscope, and ten fields (areas on a grid inherent to the flask) are examined using the 10× objective. In general, the ten fields should be non-contiguous, or significantly removed from one another, so that the ten fields are a representative sampling of the whole flask. Percentage cell occupancy for each field examined is noted, and averaging of these percentages then provides an estimate of overall percent confluency in the cell culture. When patient samples have been divided between two or among three or more flasks, an average cell count for the total patient sample should be calculated. The calculated average percent confluency should be entered into a process log to enable compilation of data—and plotting of growth curves—over time. Alternatively, confluency may be judged independently for each flask. Monolayer cultures may be photographed to document cell morphology and culture growth patterns. The applicable formula is:

$$\text{Percent confluency} = \frac{\text{estimate of the area occupied by cells}}{\text{total area in an observed field}}$$

As an example, therefore, if the estimate of area occupied by the cells is 30% and the total area of the field is 100%, percent confluency is 30/100, or 30%.

Following initial culturing of the multicellular tissue explant, the tissue explant is removed from the growth medium at a predetermined time. In one embodiment, the explant is removed from the growth medium prior to the emergence of a substantial number of stromal cells from the explant. Alternatively, the explant may be removed according to the percent confluency of the cell culture. In one embodiment of the invention, the explant is removed at about 10 to about 50 percent confluency. In a preferred embodiment of the invention, the explant is removed at about 15 to about 25 percent confluency. In a particularly preferred embodiment, the explant is removed at about 20 percent confluency. By removing the explant in either of the above manners, a cell culture monolayer predominantly composed of target cells (e.g., tumor cells) is produced. In turn, a substantial number of non-target cells, such as fibroblasts or other stromal cells, fail to grow within the culture. Ultimately, this method of culturing a multicellular tissue explant and subsequently removing the explant at a predetermined time allows for increased efficiency in both the preparation of cell cultures and subsequent assays of various agents using the cultures. Adaptation of the above protocol for non-tumor cells is straightforward and generally constitutes an equivalent procedure.

The essence of the invention thus includes the important feature of the simplicity of the present system—cohesive multicellular explants of the patient tissue to be tested are used to form cell monolayers; growth of those monolayers may be monitored for accurate prediction of correlating growth of the same cells in vivo; explants are removed from the growth medium at a predetermined time, and differing concentrations of a number of active agents may be tested for the purpose of determining chemosensitivity of the tissue sample and the most appropriate agent and concentration of that agent for actual patient exposure (according to the calculated cell growth rates). It is also important to note, in the context of the invention, that the present system allows in vitro tests to be conducted in suspensions of tissue culture monolayers grown in nutrient medium under fast conditions (a matter of weeks), rather than with single cell progeny produced by dilution cloning over long periods of time. In some cases, the present invention provides a cell culture for a two stage assay for both cytotoxicity and the longer-term growth inhibitory.

EXAMPLE

Chemosensitivity Assay

Methods of the invention include methods for determining the efficacy of an active agent. The performance of the chemosensitivity assay used for screening purposes depends on the ability to deliver a reproducible cell number to each row in a plate and/or a series of plates, as well as the ability to achieve an even distribution of cells throughout a given well. The following exemplary procedure assures that cells are reproducibly transferred from flask to microtiter plates, and cells are evenly distributed across the surface of each well.

An initial step in preparing the microtiter plates is preparing and monitoring the monolayer as described above with the removal of the explant at 20 percent confluency. The following example shows an exemplary protocol which is susceptible of variation as will be apparent to one skilled in the art. Cells were removed from the culture flask and a cell pellet was prepared by centrifugation. The cell pellet derived from the monolayer was then suspended in 5 ml of the growth medium, mixed in a conical tube and subsequently rocked back and forth 10 times. A 30 µl droplet from the center of the conical tube was pipetted into one well of a 96 well plate. A fresh pipette was then used to pipette a 30 µl aliquot of trypan blue solution, which was added to the same well, and the two droplets were mixed with repeated pipette aspiration. The resulting admixture was then applied to a hemocytometer chamber for examination using a standard light microscope. Cells were counted in all of four hemocytometer quadrants, under 10× magnification. Only those cells which had not taken up the trypan blue dye were counted. Using means known in the art, the quadrant count values were checked, logged, multiplied by $10^4$ to give cells/ml, and the total amount of fluid (growth medium) necessary to suspend remaining cell aliquots was calculated accordingly.

After the desired concentration of cells in medium has been determined, additional cell aliquots from the monolayer were suspended in growth medium via rocking and then, loaded into a Terasaki dispenser. Aliquots of the prepared cell suspension were delivered into the microtiter plates using Terasaki dispenser techniques known in the art. Alternatively, an electronic multichannel pipettor commercially available from Matrix Technology Corp. may be used. A plurality of plates may be prepared from a single cell suspension as needed. Plates were subsequently incubated in an incubator box by means known in the art. Upon preparation of the cell suspension, cells from the suspension may be inoculated into segregated sites for subsequent assays. At least one agent may be exposed to the segregated sites to determine the chemosensitivity of the tissue samples, as well as the therapeutic or chemotherapeutic effects of the agents on the tissue sample.

The following example provides an exemplary protocol for assaying active agents in accordance with the invention. During this portion of the inventive assay, the appropriate amount of specific active agent was transferred into the microtiter plates prepared as described above. A general protocol, which may be adapted, follows. Each microtiter plate was microscopically examined for cell adhesion. Control solution was dispensed into delineated rows of wells within the grid in the microtiter plate, and appropriate aliquots of active agent to be tested were added to the remaining wells in the remaining rows. Ordinarily, sequentially increasing concentrations of the active agent being tested were administered into progressively higher numbered rows in the plate. The plates were then incubated in an incubator box at 37° C. under 5% $CO_2$. After a predefined exposure time, the plates were blotted with sterile gauze to remove the agent, washed with Hank's Balance Salt Solution, flooded with growth medium, and replaced in the incubator in an incubator box for a predefined time period, after which the plates were fixed and stained for evaluation.

Fixing and staining may be conducted according to a number of suitable procedures; the following is representative. After removal of the plates from the incubator box, culture medium were poured off and the plates were flooded with Hank's Balance Salt Solution. After repeated flooding (with agitation each time) the plates were then flooded with reagent grade ethanol for 2-5 minutes. The ethanol was then poured off. Staining was accomplished using a DAPI (4',6-diamidino-2-phenylindole, dilactate) staining method. Each plate was flooded with a DAPI/water solution, with a concentration of about 400 nM, and allowed to stand for at least 10 minutes, after which the DAPI/water was poured into a beaker. The plates were then dipped into a beaker of running water to remove the excess DAPI. Cells per well may then be counted manually or by automated and/or computerized means, to derive data regarding chemosensitivity of cells at various concentrations of exposure. One particularly useful computer operating environment for counting cells is the commercially available Zeiss Axiovert S100 Automatic Inverted Flourescence Microscope and Computer.

The above procedures do not change appreciably when cell growth promoters are assayed rather than cell arresting agents such as chemotherapeutic agents. The present assay allows cell death or cell growth to be monitored with equal ease. In any case, optimization of use of the present system will involve the comparative testing of a variety of candidate active agents, for selection of the best candidate for patient treatment based upon the in vitro results. One particularly advantageous embodiment of the above-described invention comprises a two-stage assay for cytotoxicity followed by evaluation of longer-term inhibitory effect. Chemotherapeutic agents may thus be evaluated separately for both their direct chemotherapeutic effect as well as for their longer duration efficacy.

The invention is not to be limited only to the illustrative description provided herein. Variations, modifications, and other implementations of what is described herein will occur to those of ordinary skill without departing from the spirit and scope of the invention.

What is claimed is:

1. A method for assessing a response of tumor cells to an agent comprising:
   (a) culturing a plurality of multicellular tumor tissue explants from a patient specimen in the presence of growth medium, so as to allow for growth of tumor cells into a monolayer;
   (b) monitoring growth and morphology of the monolayer, and removing said explants from said growth medium when the monolayer is at about 10 to about 50 percent confluency and then growing the monolayer;
   (c) suspending cells of said monolayer and inoculating the suspended cells in a plurality of segregated sites;
   (d) treating each of the plurality of segregated sites with at least one active agent; and
   (e) measuring the response of the cells in said plurality of sites to the at least one active agent, thereby assessing a response of the tumor cells.

2. The method of claim 1, wherein the multicellular tumor tissue explants are prepared by mechanically fragmenting a tumor tissue sample.

3. The method of claim 1, wherein the growth medium is substantially free of enzymes capable of digesting said explants.

4. The method of claim 1, wherein the stromal cells are fibroblasts.

5. The method of claim 2, wherein the tumor tissue sample is at least about 100 mg.

6. The method of claim 1, wherein the multicellular tumor tissue explants measure about 1 $mm^3$.

7. The method of claim 1, wherein the percent confluency is determined by estimating an area of an observed field occupied by the monolayer.

8. The method of claim 1, wherein the growth and/or cell morphology of the monolayer is monitored by phase contrast microscopy.

9. The method of claim 1, wherein cell death in response to the at least one active agent is determined.

10. A method for predicting a response of a cancer patient to a plurality of candidate treatments, the method comprising:
    preparing a plurality of multicellular tumor tissue explants from a cancer patient specimen;
    culturing the multicellular tumor tissue explants in the presence of growth medium, so as to allow for growth of tumor cells into a monolayer;
    monitoring growth and morphology of the monolayer, and removing the explants from the growth medium when the monolayer is at about 10 to about 50 percent confluency and then growing the monolayer;
    suspending the cells of said monolayer and inoculating the suspended cells in a plurality of segregated sites;
    treating each of the plurality of segregated sites with a candidate treatment; and
    measuring the response of the cells in said plurality of sites to the candidate treatments, thereby predicting a response of the cancer patient to each of the plurality of candidate treatments.

11. The method of claim 10, wherein the multicellular tumor tissue explants are prepared by mechanically fragmenting a tumor tissue sample.

12. The method of claim 10, wherein the growth medium is substantially free of enzymes capable of digesting said explant.

13. The method of claim 10, wherein the stromal cells are fibroblasts.

14. The method of claim 10, wherein the tumor tissue sample is at least about 100 mg.

15. The method of claim 10, wherein the multicellular tumor tissue explants measure about 1 $mm^3$.

16. The method of claim 10, wherein the percent confluency is determined by estimating an area of an observed field occupied by the monolayer.

17. The method of claim 10, wherein the growth and/or cell morphology of the monolayer is monitored by phase contrast microscopy.

18. The method of claim 10, wherein cell death in response to the plurality of active agents is determined.

19. The method of claim 10, further comprising, comparing the response of the cells to each of the plurality of active agents.

20. The method of claim 1, wherein the explants are removed from the growth medium when the monolayer is at about 15% to about 25% confluency.

21. The method of claim 10, wherein the explants are removed from the growth medium when the monolayer is at about 15% to about 25% confluency.

* * * * *